(12) United States Patent
Mei et al.

(10) Patent No.: US 11,972,544 B2
(45) Date of Patent: Apr. 30, 2024

(54) METHOD AND APPARATUS FOR OPTICAL COHERENCE TOMOGRAPHY ANGIOGRAPHY

(71) Applicant: TOPCON CORPORATION, Tokyo (JP)

(72) Inventors: Song Mei, Franklin Park, NJ (US); Toshihiro Mino, West New York, NJ (US); Dawei Li, Oakland, NJ (US); Zaixing Mao, Tokyo (JP); Zhenguo Wang, Ridgewood, NJ (US); Kinpui Chan, Ridgewood, NJ (US)

(73) Assignee: TOPCON CORPORATION, Tokyo (JP)

( * ) Notice: Subject to any disclaimer, the term of this patent is extended or adjusted under 35 U.S.C. 154(b) by 407 days.

(21) Appl. No.: 17/318,233

(22) Filed: May 12, 2021

(65) Prior Publication Data

US 2021/0358096 A1    Nov. 18, 2021

Related U.S. Application Data

(60) Provisional application No. 63/024,800, filed on May 14, 2020.

(51) Int. Cl.
*G06T 5/50* (2006.01)
*A61B 5/00* (2006.01)
(Continued)

(52) U.S. Cl.
CPC .............. *G06T 5/50* (2013.01); *A61B 5/0066* (2013.01); *A61B 5/0261* (2013.01); *A61B 5/489* (2013.01); *A61B 5/7267* (2013.01); *A61B 5/742* (2013.01); *G01B 9/02041* (2013.01); *G01B 9/02091* (2013.01); *G06T 7/33* (2017.01); *G06T 2200/04* (2013.01); *G06T 2207/10101* (2013.01);
(Continued)

(58) Field of Classification Search
CPC ......... G06T 5/50; G06T 7/33; G06T 2200/04; G06T 2207/10101; G06T 2207/20081; G06T 2207/20221; G06T 2207/30104; A61B 5/0066; A61B 5/0261; A61B 5/489; A61B 5/7267; A61B 5/742; G01B 9/02041; G01B 9/02091
See application file for complete search history.

(56) References Cited

U.S. PATENT DOCUMENTS

| 2018/0199809 A1* | 7/2018 | Artsyukhovich | ...... A61B 3/102 |
| 2020/0273214 A1* | 8/2020 | Xu | ........................... G06N 3/08 |
| 2022/0151490 A1* | 5/2022 | Jia | ........................... A61B 3/102 |

OTHER PUBLICATIONS

Lo et al, "Machine Learning for Optical Coherence Tomography Angiography", 2019, Proc. of SPIE-OSA (ECBO) vol. 11078 (3 Pages) (Year: 2019).*

(Continued)

*Primary Examiner* — David F Dunphy
(74) *Attorney, Agent, or Firm* — Pearne & Gordon LLP (57) ABSTRACT

Optical coherence tomography (OCT) angiography (OCTA) data is generated by one or more machine learning systems to which OCT data is input. The OCTA data is capable of visualization in three dimensions (3D) and can be generated from a single OCT scan. Further, motion artifact can be removed or attenuated in the OCTA data by performing the OCT scans according to special scan patterns and/or capturing redundant data, and by the one or more machine learning systems.

20 Claims, 4 Drawing Sheets

(51) Int. Cl.
  *A61B 5/026* (2006.01)
  *G01B 9/02* (2022.01)
  *G01B 9/02091* (2022.01)
  *G06T 7/33* (2017.01)

(52) U.S. Cl.
  CPC ............... *G06T 2207/20081* (2013.01); *G06T 2207/20221* (2013.01); *G06T 2207/30104* (2013.01)

(56) References Cited

OTHER PUBLICATIONS

Extended European Search Report for European Application No. 21173929.7 dated Oct. 8, 2021.

Liu et al, "A deep learning based pipeline for optical coherence tomography augiography", Journal of Biophotonics, vol. 12, No. 10, 1 pp. 1-10, Oct. 2019, XP055845198, ISSN: 1864-063X, DOI: 10.1002/ibio.201900008.

Jiang et al., "Comparative study of deep learning models for optical coherence tomography angiography", Biomedical Optics Express, vol. 11, No. 3, pp. 1580-1597, Feb. 26, 2020, XP055675654, United States, ISSN: 2156-7085, DOI: 10.1364/BOE.387807.

Hossbach et al., "Deep OCT Angiography Image Generation for Motion Artifact Suppression", arxiv.org, arXiv:2001.02512v1 pp. 1-6, Jan. 8, 2020, XP081500380, DOI: 10.1007/978-3-658-29267-6_55.

Yang et al., "Deep learning enables extraction of capillary-level angiograms from single OCT volume", arxiv.org, arXiv:1906.07091v2, pp. 1-3, Jun. 17, 2019, XP81500380.

Lee et al., "Generating retinal flow maps from structural optical coherence tomography with artificial intelligence", Nature Scientific Reports, 9:5694, pp. 1-11, Apr. 5, 2019, XP055845164, DOI:10.1038/s41598-019-42042-y.

Lo et al., "Machine Learning for Optical Coherence Tomography Angiography", Proceedings of SPIE-OSA, vol. 11078, pp. 110781-1-110781-3, Jun. 23-25, 2019, XP0601123674, ISSN: 1605-7422, DOI: 10.1117/12.2527210 ISBN: 978-1-5106-0027-0.

Abdolmanafi et al., "Intra-Slice Motion Correction of Intravascular OCT Images Using Deep Features", IEEE Journal of Biomedical and Health Informatics, vol. 23, No. 3, pp. 931-941, May 1, 2019, XP011722658, ISSN: 2168-2194, DOI: 10.1109/JBHI.2018.2878914.

Kraus et al., "Motion correction in optical coherence tomography vols. on a per A-scan basis using orthogonal scan patterns", Biomedical Optics Express, vol. 3, No. 6, pp. 1182-1199, Jun. 1, 2012.

Hartinger et al., "Monte Carlo modeling of angiographic optical coherence tomography", Biomedical Optics Express, vol. 5, No. 12, pp. 1-12, Dec. 2014.

Chen et al., "Three-dimensional eye motion by Lissajous scan optical coherence tomography", Biomedical Optics Express, vol. 8, No. 3, pp. 1783-1802, Mar. 1, 2017.

Chen et al., "Eye-motion-corrected optical coherence tomography angiography using Lissajous scanning", Biomedical Optics Express, vol. 9, No. 3, pp. 1111-1129, Mar. 1, 2018.

Yyasuno et al., "Motion-free optical coherence tomography angiography by Lissajous scan", Invest. Ophthalmol. Vis. Sci. 2018;59(9):2852. doi: https://doi.org/. (Abstract Only).

Camino et al., "Evaluation of artifact reduction in optical coherence tomography angiography with real-time tracking and motion correction technology", Biomedical Optics Express, vol. 7, No. 10, pp. 3905-3915, Oct. 2016.

\* cited by examiner

METHOD AND APPARATUS FOR OPTICAL COHERENCE TOMOGRAPHY ANGIOGRAPHY

CROSS-REFERENCE TO RELATED APPLICATIONS

This application claims priority to U.S. Provisional Patent Application No. 63/024,800 filed on May 14, 2020, the entirety of which is incorporated herein by reference.

BACKGROUND

Current optical coherence tomography angiography (OCTA) is essentially limited to two-dimensional (2D) visualization and quantification. Generating the OCTA data involves capturing volumetric (3D) OCT data of an imaged object at two or more relatively close points in time. These pairs of volumetric OCT data can be registered to each other, and then the OCTA data can be generated as a difference or ratio (or like decorrelation) between common locations of the object in the OCT data. This decorrelation corresponds to the flow of blood. And because (with the exception of leakage) blood flow is within structural blood vessels (hereinafter 'vasculature'), the decorrelation and blood flow can be a proxy for identifying vasculature. However, the decorrelation does not identify the vasculature itself, and thus the OCTA data itself does not necessarily include vasculature information. In other words, structural vessel information is lost in the conversion from OCT data to OCTA data. The 2D visualizations of the OCTA data (showing location and properties of blood flow, and thus implying location and properties of vasculature) are then formed as (max-) projection images of a slab in the volumetric OCTA data, where the slab is defined by segmentation the volume. However, segmentation is prone to errors, which affect visualization. Further, three-dimensional (3D) vessel structural information is also lost within each defined slab due to the projection.

These limitations to OCTA are due in part to current OCTA volumes being too noisy to visualize directly in 3D, thus requiring visualizations in the form of the projection images. Additionally, motion (white-line) artifact is prevalent in the data, which is easier to neutralize in 2D than in 3D. Still further, projection artifact, which is inherent to OCTA, can limit the usability of 3D visualizations without 3D projection artifact removal performed on the 3D data.

More particularly regarding quality, as noted above, conventional OCTA generation utilizes the difference or ratio of two or more OCT scans, or otherwise determine a decorrelation between two or more OCT scans. These decorrelation processes, however, can induce the above-noted projection artifact inherent to OCTA. Additionally, each scan can include different speckle/random noise from the OCT system, resulting in noisy OCT data and even noisier OCTA data. Further, OCTA image quality is largely affected by OCT intensity, and intensity is not uniform throughout the volume. Still further, because sensitivity for flow signals is directly dependent on inter-scan time, variations in inter-scan time can induce artifacts. For example, a short interscan time may be insufficient to capture changes cause by blood flow; however, a long interscan time can result in motion artifact and saturation of faster blood flows.

Motion artifacts are introduced because the imaged object may move between each OCT scan (during the inter-scan time). Conventional motion correction techniques generally fall into one of two categories: re-scan based correction (tracking of the object to identify movement thereof for removal), and post-processing based correction. Tracking requires additional expensive hardware to monitor the movements of the object, so that they can be accounted for in the resulting OCTA data. For example, such hardware may include infrared (IR) or scanning laser ophthalmology (SLO) imaging equipment. In addition to the cost and complexities of this hardware, correction is limited to the speed of the tracking system (e.g. 30 Hz for IR). While post-processing correction does not require this hardware and allows for axial motion correction, the post-processing corrections utilize computationally expensive registration algorithms (for matching the repeated scans). Further, correlation-based registration algorithms lack accuracy and success rates. As a result, OCTA volumes will have missing pixels when registration fails.

BRIEF SUMMARY

According to one example of the present disclosure, an imaging method comprises: obtaining redundant optical coherence tomography (OCT) data of an object with a Lissajous, orthogonal, or parallel scanning pattern; inputting the redundant OCT data to at least one trained machine learning system; registering or merging the redundant OCT data by the at least one trained machine learning system; and generating three-dimensional (3D) OCT angiography (OCTA) data by the at least one trained machine learning system, the 3D OCTA data being an output from the at least one trained machine learning system, wherein the trained machine learning system is trained to identify structural vasculature information and blood flow information in the redundant OCT data, and wherein the 3D OCTA data comprises the identified structural vasculature information and the identified blood flow information.

In various embodiments of the above example, the redundant OCT data is a plurality of B-frames from a same location of the object; the redundant OCT data is a plurality of volumes of the object; the redundant OCT data comprises a plurality of scan pairs of OCT data from a same location of the object; the at least one machine trained machine learning system is a single machine learning system trained to register or merge the redundant OCT data and to output the 3D OCTA data; the at least one trained machine learning system comprises: a first trained machine learning system configured to receive the redundant OCT data and to output registered or merged OCT data, and a second trained machine learning system configured to receive the registered or merged OCT data and to output the 3D OCTA data; ground truth training data for the at least one machine learning system comprises results from a Monte Carlo simulation; ground truth training data for the at least one machine learning system comprises OCTA B-frames generated by determining a difference or ratio between repeated OCT scans at a same location of the object; ground truth training data for the at least one machine learning system comprises angiographic B-frames or volumes generated from an imaging modality other than OCT; the method further comprises: obtaining second 3D OCTA data of the object, inputting the generated 3D OCTA data and the second 3D OCTA to a longitudinal machine learning system trained to register the second 3D OCTA data to the generated 3D OCTA data and output the registered 3D OCTA data, and determining a structural change in the object based on the registered 3D OCTA data; and/or the method further comprises generating a 3D visualization of the object based on the 3D OCTA data.

According to another example of the present disclosure, an imaging method comprises: obtaining optical coherence tomography (OCT) data from a single scan of the object; inputting the OCT data from the single scan to at least one trained machine learning system; and generating three-dimensional (3D) OCT angiography (OCTA) data by the at least one trained machine learning system, the 3D OCTA data being an output from the at least one trained machine learning system, wherein the trained machine learning system is trained to identify structural vasculature information in the OCT data from the single scan, and wherein the 3D OCTA data comprises the identified structural vasculature information.

In various embodiments of the above example, the single scan of the object follows a Lissajous, orthogonal, or parallel scanning pattern; the OCT data comprises a plurality of scan pairs of OCT data from a same location of the object; ground truth training data for the at least one machine learning system comprises results from a Monte Carlo simulation; ground truth training data for the at least one machine learning system comprises OCTA B-frames generated by determining a difference or ratio between repeated OCT scans at a same location of the object; ground truth training data for the at least one machine learning system comprises angiographic B-frames or volumes generated from an imaging modality other than OCT; the method further comprises: obtaining second 3D OCTA data of the object, inputting the generated 3D OCTA data and the second 3D OCTA to a longitudinal machine learning system trained to register the second 3D OCTA data to the generated 3D OCTA data and output the registered 3D OCTA data, and determining a change in the object based on the registered 3D OCTA data; and/or the method further comprises generating a 3D visualization of the object based on the 3D OCTA data.

DETAILED DESCRIPTION OF THE DRAWING

Based on the foregoing, the present disclosure relates to OCTA data generation techniques, for example, that allow for 3D OCTA visualization. More particularly, OCT data quality is addressed by utilizing machine learning systems for OCTA generation, and motion artifacts are removed by utilizing special scan patterns combined with machine learning based post-processing techniques.

Briefly, OCTA generation with machine learning comprises inputting OCT data to a trained machine learning system, which then outputs OCTA data. The OCT data may be individual OCT B-frame images, neighboring B-frame images (e.g., registered to each other), C-frame images, projection images, and/or 3D OCT images/volumes (collections of B- or C-frame images). Similarly, the output OCTA data may be individual OCTA B-frame images, C-frame images, projection images, and/or 3D OCTA images/volumes (collections of B- or C-frame images).

The use of machine learning systems to generate OCTA data provides many benefits over traditional OCTA generation techniques. For example, machine learning OCTA generation produces the same or better image quality to conventional techniques, and is able to generate original or averaged (or otherwise denoised) OCTA data and subsequent visualizations. Additionally, machine-learning OCTA generation can produce OCTA data with no or reduced motion artifact caused by motion of the imaged object between repeated scans, and can incorporate the effects of many processing techniques. This is because the machine learning systems are based on complex convolutions of image data, and which are not necessarily affected by the motion. In contrast, conventional OCTA generation relies on simple differences between the repeated scans, which are directly induced by motion. Still further, machine learning techniques can reduce dependency on input OCT image intensity and inter-scan time. Again, complex convolutions regulate changes in OCT intensity and produce more consistent OCTA images. This also relaxes dependency on inter-scan time for flow detection sensitivity.

In addition to the above, it is also possible to generate OCTA data without repeated scans. Rather, the OCTA data can be generated from OCT data captured during a single scan, or by neighboring (registered) OCT images. Because conventional OCTA techniques require a difference between repeated scans, OCTA generation from single OCT volumes is not possible. And because the vasculature can be identified without determining a decorrelation, the OCTA data resulting from the machine learning system does not include any projection artifact. OCTA generation from a single scan is possible because the machine learning systems can be trained to recognize structural differences between vasculature and other tissues, and those structural differences are present in individual scans of OCT data. For example, blood vessels may cast shadow in OCT B-scans and the blood vessel themselves may appear as hyperreflective (high intensity) compared to neighboring tissues. These features may not be identifiable without machine learning (e.g., with traditional image processing techniques) due to current limitations in imaging resolution. Further, although flow speed may not be detected directly with single scans, the speed may be inferred from the size of the vessel. Thus, determinations about flow speed may also be made the machine learning system. In contrast, conventional techniques recognize blood flow (via differences, ratios, and other decorrelations between pairs of scans) as a proxy for identifying the vasculature.

Notwithstanding the above, pairs of scans can also be input to the machine learning system according to the present disclosure in order to determine blood flow, and further enhance identification of vasculature. Accordingly, the machine learning system can additionally or alternatively be trained to identify differences between pairs (two or more scans) of scan data from a same location of the image object, with those differences corresponding to blood flow. Such determinations can enhance the identification of vasculature made in individual scan data and also more directly determine properties of the blood flow itself. And as above, because the trained machine learning system does not itself utilize the decorrelation processes that inherently introduce projection artifact, machine learning generated OCTA data from pairs of data may also not include the projection artifact found in OCTA data generated by traditional techniques.

As a result of the above, OCTA data generated by machine learning systems can include structural vasculature information and/or blood flow information. In other words, the machine learning system is trained to identify structural vasculature information and/or blood flow information. In contrast, as noted above, traditional OCTA data only includes blood flow information because the structural vasculature is not identified through decorrelation techniques. With both the vessel structure and blood flow information, it is possible to identify blood vessels lacking flow, and blood flow leakage (flow not necessarily in any vessel). Further, the separate vasculature and flow information can supplement each other so that each can be more accurately identified.

Still further, motion artifact can be reduced by capturing the OCT data that is input to the OCTA generation machine learning systems with special scan patterns. These special scan patterns can eliminate the need for tracking any motion of the imaged object. And the use of additional machine learning post-processing can eliminate the above-noted algorithm limitations for registration (e.g., computation time, accuracy, and success rate). For example, the special scan patterns may include scan patterns that follow Lissajous curves, orthogonal scan patterns, repeated parallel scan patterns, and the like. Orthogonal scan patterns may be those in which a first direction (e.g., along the X-axis) is the fast-scanning axis and a second orthogonal direction (e.g., along the Y-axis) is the slow-scanning axis, and then the scan is repeated where the second orthogonal direction is the fast axis and the first direction is the slow axis. Similarly, parallel scan patterns may repeat scans with the same directions as the fast and slow axes. Scans according to these patterns may be taken two or more times to produce redundant information, which can be used to identify and correct motion artifact.

Redundant scans according to these patterns can take advantage of the relative differences between scanning speed in the direction dictated by the scan pattern, and the motion of the object that would induce motion artifact. For example, it can be assumed that motion is negligible along the fast-scanning axis (or direction). Taking the orthogonal scan as an example, the scan pattern produces first scan data in which data along the X-axis (e.g., the first fast scan direction) is not affected by motion artifact, and another scan data in which data along the Y-axis (e.g., the second scan direction) is not affected by motion artifact. These data can then be combined (merged) to eliminate or reduce the motion artifact. Similarly, it can be assumed that the same motion will not occur during subsequent scans. For example, the parallel scan produces two scans in which the only differences should be motion. Because motion of the object can be identified by outlier or missing data (which is distinguishable from blood flow motion, which would otherwise look normal), the motion artifact data in the first scan can be replaced by the corresponding location data in the redundant scan. In still other embodiments, data from redundant scans (of any pattern) can be averaged or otherwise combine according to any method. In instances where data is missing due to motion, the redundant scan can add the missing information; and in instances where no data is missing, averaging or like statistical techniques can improve image quality.

The redundant information may include redundant A-line scans at each pixel location, which are then registered to each other or merged together (e.g., as discussed above). Redundant information may also be collected at the B-scan or C-scan levels. These redundant scans are not to be confused with scan pairs used to determine blood flow, which can be distinguished by the relative different time frames each 'motion' occurs. For example, generally, scan pairs for determining blood flow are taken with a relatively short interscan time (e.g., by scanning an A-line at least twice prior to advancing to the next pixel location, or repeating scans along the fast scanning direction prior to advancing along the slow scanning axis), whereas redundant scans for identifying and correcting motion artifact are taken with a relatively long interscan time (e.g., after a complete scan according to the scan pattern). In these cases, the underlying OCT data would include a plurality of pairs of OCT scan data, each pair of scan data being useful for identifying blood flow between the scans of the pair, and the plurality of pairs at each location being useful to determine motion artifact. However, because blood flow motion and motion artifact manifest differently in the underlying OCT data (e.g., the motion artifact being outlier or missing data), it may be possible to utilize the scan pairs for determining blood flow as the redundant scan data.

The above discussed plurality of scans can be registered to each other in various ways. For example, scan pairs for identifying blood flow can be registered to each other based on structural information. Redundant scans can similarly be registered with each other. Where scan pairs and redundant scans are both taken, the scan pairs can be registered with each other, each scan pair being treated as a single 'unit'. Still further, all scans can be registered with each other.

In some embodiments, the above identification of motion can be performed by a trained machine learning system. For example, the machine learning system may be trained to identify the expected differences between subsequent scans along one of the special scan patterns, or between redundant scans at the same location. In other words, the machine learning system may be trained to identify structural differences (e.g., of a vessel) in OCT scan data that can be attributed to motion of the imaged object, rather than differences cause by blood flow (e.g., within a vessel).

Figure 1:
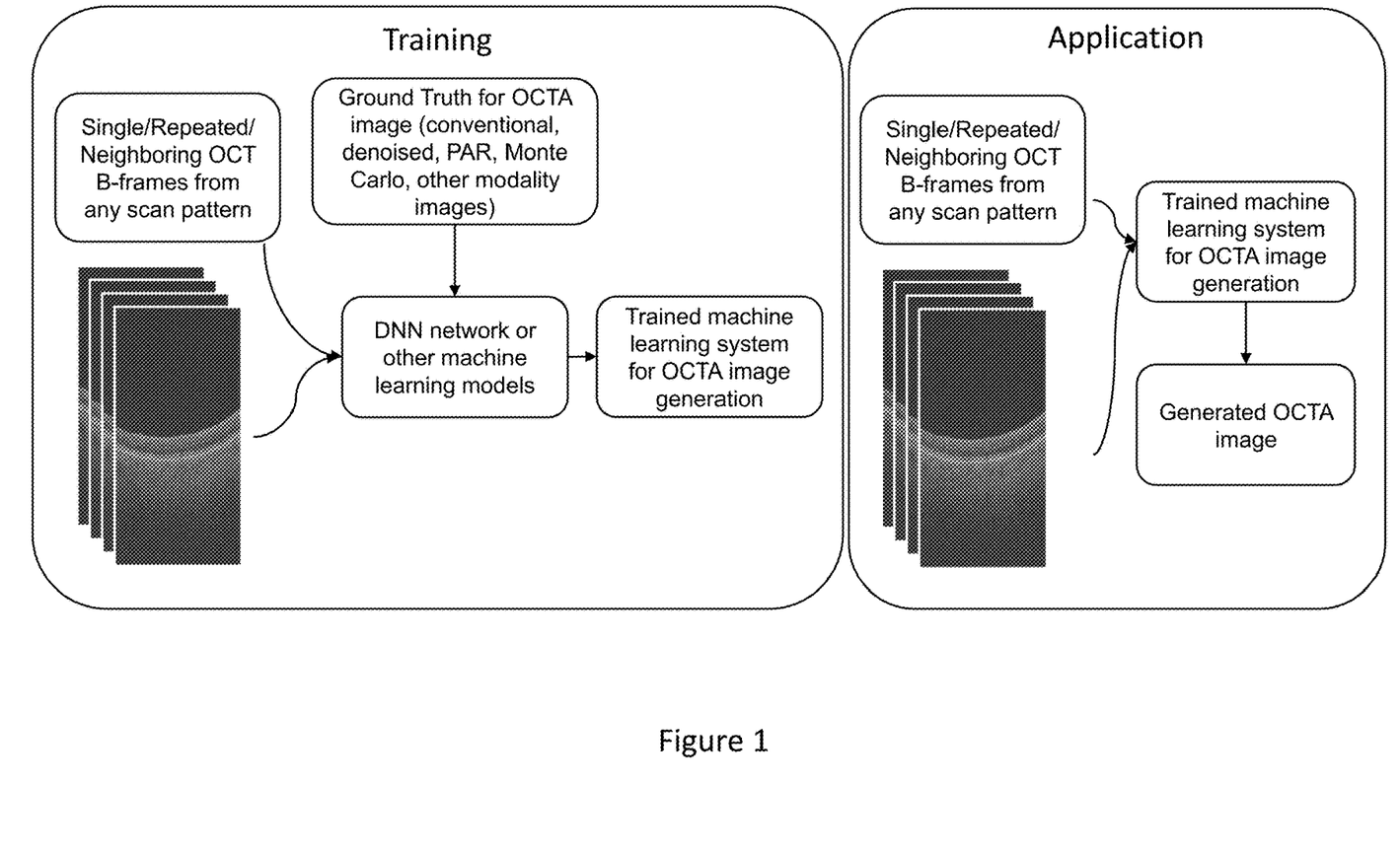
FIG. 1 illustrates a first example imaging process.

The following disclosure relates to example imaging processes in accordance with the above description. A first example process for generating OCTA data is illustrated in FIG. 1. According to the example of FIG. 1, training an OCTA generation machine learning system includes inputting single, repeated, and/or neighboring OCT B-scan images to a deep neural network (DNN) or like machine learning model. The OCT B-scan images may be captured according to any scan pattern. Ground truth OCTA images (the known angiographic data corresponding to the input OCT data) are also input the machine learning model. This supervised learning produces a trained machine learning system that outputs OCTA data from the input OCT data. In use then, single, repeated, and/or neighboring OCT B-scan images from any scan pattern may be input to the trained machine learning system, which then outputs a corresponding OCTA data.

Figure 2:
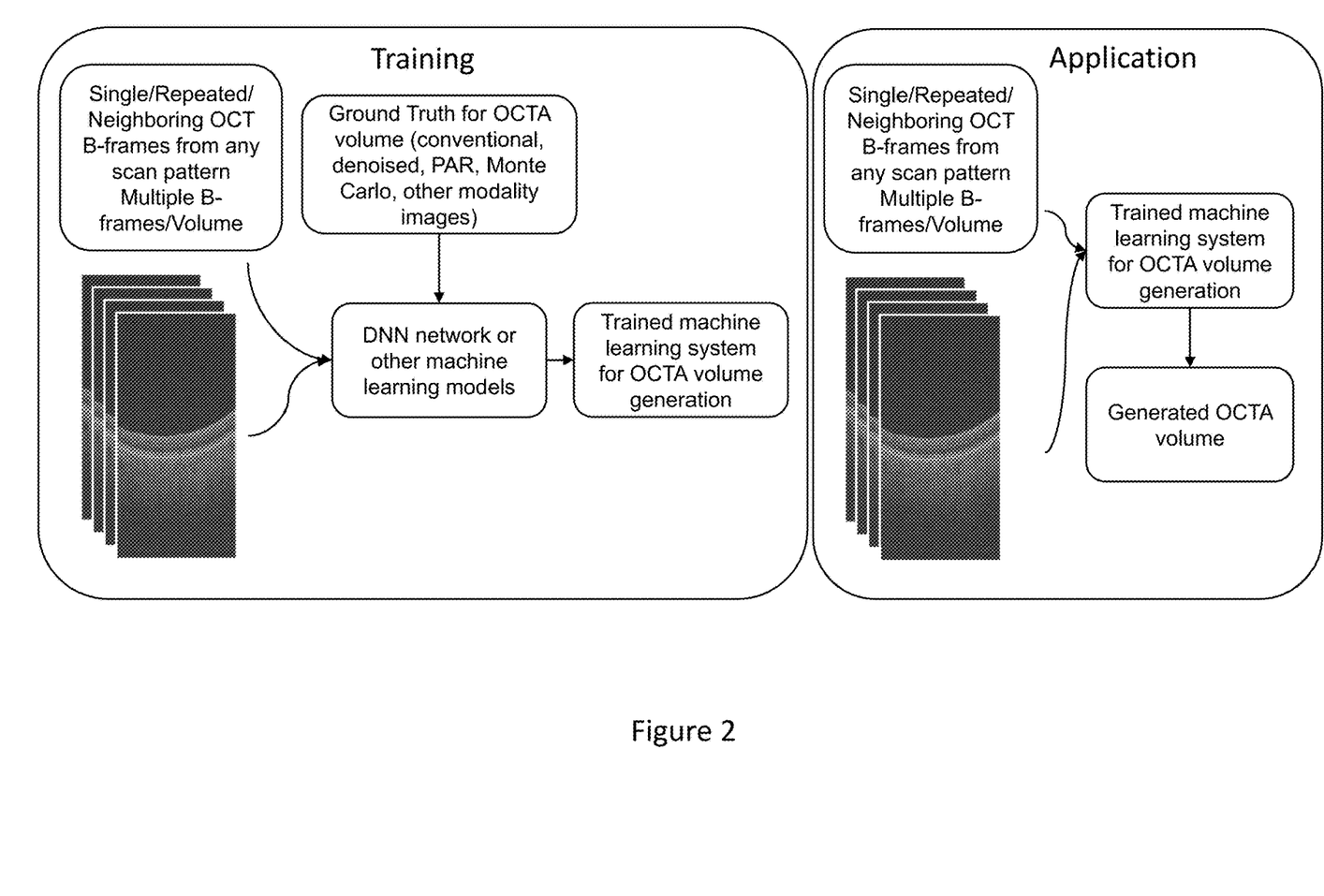
FIG. 2 illustrates a second example imaging process.

Another example OCTA generation process is shown in FIG. 2. Therein, the OCTA generation is volume-based, rather than the image-based approach shown in FIG. 1. The process in FIG. 2 is the same as in FIG. 1, however, multiple B-scan images (volumes) are input rather than individual B-scan images. As a result, the output of the machine learning system is an OCTA volume, rather than a single OCTA image. As noted above, the output OCTA volumetric data may is of sufficient quality for 3D visualization and quantification.

Figure 3:
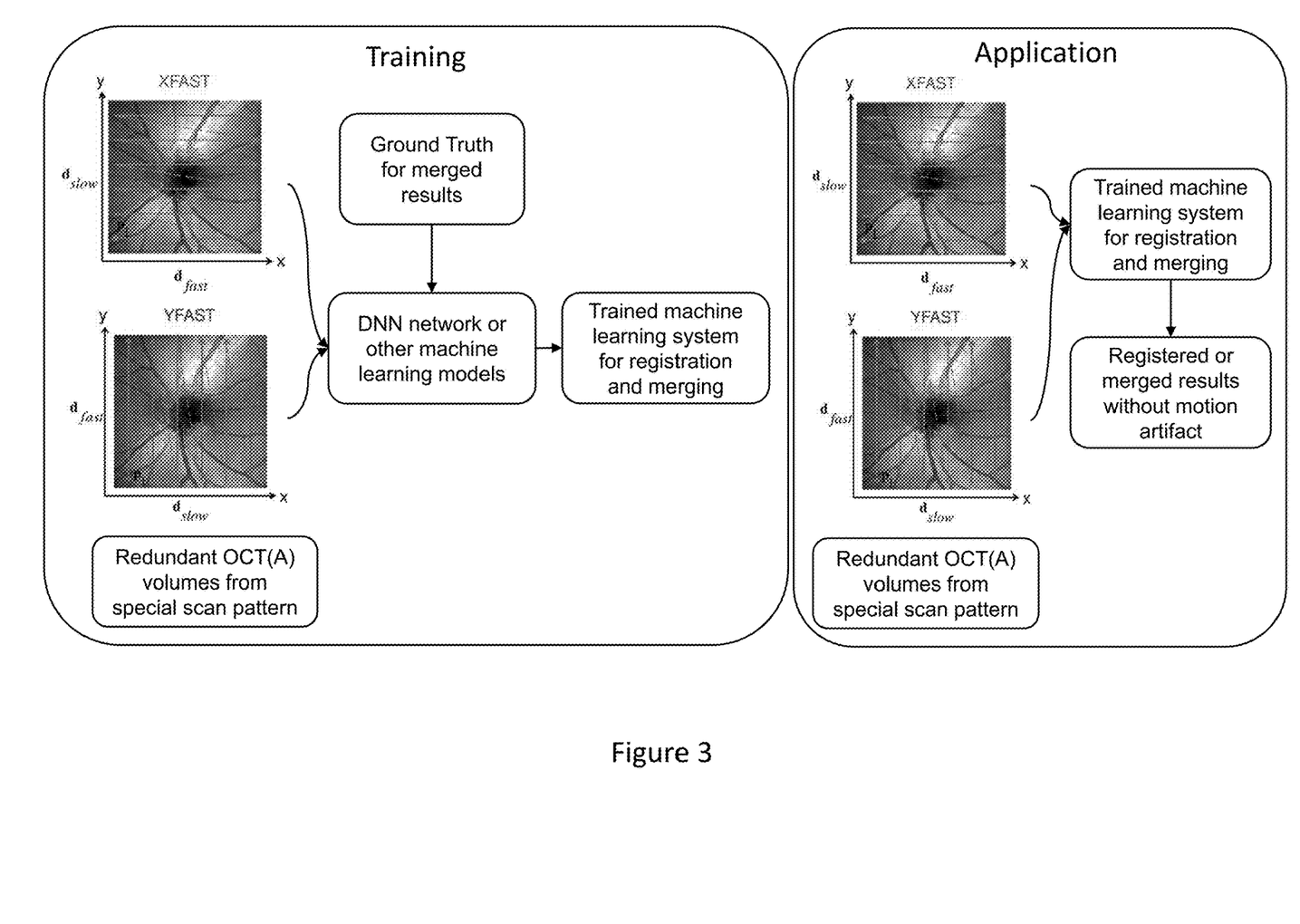
FIG. 3 illustrates a third example imaging process.

The example process illustrated in FIG. 3 is for registering or merging OCT or OCTA data. As seen therein, training the machine learning system comprises capturing redundant OCT or OCTA volumes according to a special scan pattern (shown as an orthogonal pattern in FIG. 1), and inputting the redundant volumes to a DNN or like machine learning model. Ground truth results of the registered or merged OCT or OCTA data is also input to the machine learning model for supervised training. In this example, the OCT and OCTA volumes can be generated either conventionally or via another machine learning system (e.g., according to the processes of FIGS. 1 and 2). Then during use, redundant OCT or OCTA data is captured according to a special scan pattern (again illustrated as an orthogonal scan pattern) and input to the trained machine learning system. The trained machine learning system can then output registered or merged OCT or OCTA data, having motion artifacts removed or attenuated.

In some embodiments, a machine learning system for registration or merging may be trained to receive longitudinal data. Such longitudinal data may be OCT or OCTA data of a subject captured, for example, at different clinical visits (e.g., during a follow-up appointment). These longitudinal collections of data (and their registration or merging) can be used to track disease progressions and changes over periods of time longer than those used to identify angiographic flow (e.g., weeks, months, years rather than seconds). Comparison of the longitudinal data can be used to identify structural changes in the object and changes in angiographic flow. For example, a stenosis may be identified by structural changes to the blood vessels at a given location in OCT data and/or lower amounts of flow (or flow rates) at a given location in OCTA data.

Figure 4:
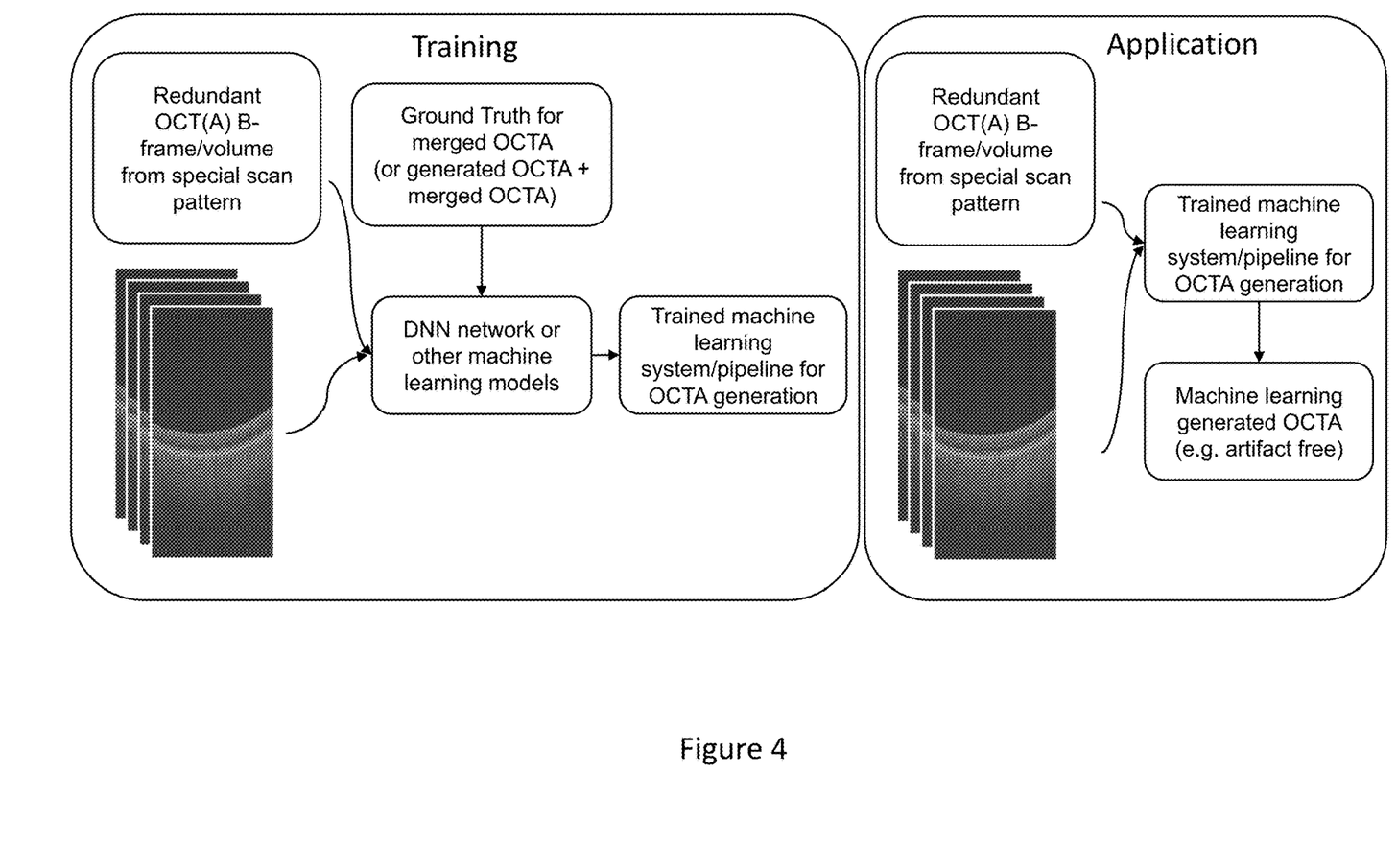
FIG. 4 illustrates a fourth example imaging process.

Finally, the example process of FIG. 4 illustrates a combined OCTA generation and registration/merging process. As shown in the figure, training the machine learning system includes inputting redundant OCT or OCTA volumes or B-frames into a machine learning system (e.g., a DNN), with ground truth OCTA (or registered/merged OCTA) data. Then during use, redundant OCT or OCTA volumes or B-frames can input to the trained system, which outputs machine learning generated OCTA volumes or images, having sufficient quality for 3D visualization with motion artifacts removed or attenuated. Here, the machine learning system may be formed as two different systems or as a single system. When formed as two different systems, the machine learning can perform OCTA generation and merging in two steps.

As noted above, training of the machine learning systems may be supervised. The ground truth for any of the above machine learning system training data may be dependent on the desired output of the machine learning system. For example, training a machine learning system for registering/merging OCT volumes and images may be with data merged according to conventional methods, or motion-free data obtained from fast imaging systems or those with tracking. For OCTA generation machine learning systems, the ground truth may similarly be based on OCTA images or volumes formed by conventional techniques. However, the ground truth may also be a registered average of multiple OCTA images or volumes from one conventional method and/or a combination of multiple OCTA images or volumes from multiple conventional methods. Further, the OCTA generation ground truth may be enhanced OCTA images (e.g., being denoised, having contrast enhancements, projection artifact removed (PAR), and the like), other angiographic modalities (e.g., fluorescence angiography, indocyanine green angiography, (adaptive optics) scanning laser ophthalmology, (adaptive optics) OCTA, visible light OCTA, and the like), and results of Monte Carlo simulations.

Where images from other modalities are used as ground truth images, the resulting OCTA data may mimic that of those modalities. As a result, the resulting OCTA images may mimic the appearance of the images from those other modalities. Because Monte Carlo simulations are based on models, ground truth generated by the simulations is truth in-fact. In contrast, experimentally collected data (i.e., from the 'real world') processed to generate angiographic images may itself include artifacts and error. Thus training data including in part or entirely Monte Carlo simulations can improve accuracy of the machine learning systems.

While various features are presented above, it should be understood that the features may be used singly or in any combination thereof. Further, it should be understood that variations and modifications may occur to those skilled in the art to which the claimed examples pertain.

What is claimed is:

1. An imaging method comprising:
   obtaining redundant optical coherence tomography (OCT) data of an object with a Lissajous, orthogonal, or parallel scanning pattern;
   inputting the redundant OCT data to at least one trained machine learning system;
   registering or merging the redundant OCT data by the at least one trained machine learning system; and
   generating three-dimensional (3D) OCT angiography (OCTA) data by the at least one trained machine learning system, the 3D OCTA data being an output from the at least one trained machine learning system,
   wherein the trained machine learning system is trained to identify structural vasculature information and blood flow information in the redundant OCT data, and
   wherein the 3D OCTA data comprises the identified structural vasculature information and the identified blood flow information.

2. The method of claim 1, wherein the redundant OCT data is a plurality of B-frames from a same location of the object.

3. The method of claim 1, wherein the redundant OCT data is a plurality of volumes of the object.

4. The method of claim 1, wherein the redundant OCT data comprises a plurality of scan pairs of OCT data from a same location of the object.

5. The method of claim 1, wherein the at least one machine trained machine learning system is a single machine learning system trained to register or merge the redundant OCT data and to output the 3D OCTA data.

6. The method of claim 1, wherein the at least one trained machine learning system comprises:
   a first trained machine learning system configured to receive the redundant OCT data and to output registered or merged OCT data; and
   a second trained machine learning system configured to receive the registered or merged OCT data and to output the 3D OCTA data.

7. The method of claim 1, wherein ground truth training data for the at least one machine learning system comprises results from a Monte Carlo simulation.

8. The method of claim 1, wherein ground truth training data for the at least one machine learning system comprises OCTA B-frames generated by determining a difference or ratio between repeated OCT scans at a same location of the object.

9. The method of claim 1, wherein ground truth training data for the at least one machine learning system comprises angiographic B-frames or volumes generated from an imaging modality other than OCT.

10. The method of claim 1, further comprising:
    obtaining second 3D OCTA data of the object;
    inputting the generated 3D OCTA data and the second 3D OCTA to a longitudinal machine learning system trained to register the second 3D OCTA data to the generated 3D OCTA data and output the registered 3D OCTA data; and determining a structural change in the object based on the registered 3D OCTA data.

11. The method of claim 1, further comprising:

generating a 3D visualization of the object based on the 3D OCTA data.

12. An imaging method comprising:

obtaining optical coherence tomography (OCT) data from a single scan of the object;

inputting the OCT data from the single scan to at least one trained machine learning system; and generating three-dimensional (3D) OCT angiography (OCTA) data by the at least one trained machine learning system, the 3D OCTA data being an output from the at least one trained machine learning system, wherein the trained machine learning system is trained to identify structural vasculature information in the OCT data from the single scan, wherein the 3D OCTA data comprises the identified structural vasculature information, and wherein ground truth training data for the at least one machine learning system comprises OCTA B-frames generated by determining a difference or ratio between repeated OCT scans at a same location of the object, or the ground truth training data for the at least one machine learning system comprises angiographic B-frames or volumes generated from an imaging modality other than OCT.

13. The method of claim 12, wherein the single scan of the object follows a Lissajous, orthogonal, or parallel scanning pattern.

14. The method of claim 12, wherein the OCT data comprises a plurality of scan pairs of OCT data from a same location of the object.

15. The method of claim 12, wherein ground truth training data for the at least one machine learning system comprises results from a Monte Carlo simulation.

16. The method of claim 12, further comprising:

generating a 3D visualization of the object based on the 3D OCTA data.

17. An imaging method comprising:

obtaining optical coherence tomography (OCT) data from a single scan of the object inputting the OCT data from the single scan to at least one trained machine learning system;

generating three-dimensional (3D) OCT angiography (OCTA) data by the at least one trained machine learning system, the 3D OCTA data being an output from the at least one trained machine learning system;

obtaining second 3D OCTA data of the object;

inputting the generated 3D OCTA data and the second 3D OCTA to a longitudinal machine learning system trained to register the second 3D OCTA data to the generated 3D OCTA data and output the registered 3D OCTA data; and determining a change in the object based on the registered 3D OCTA data, wherein the trained machine learning system is trained to identify structural vasculature information in the OCT data from the single scan, and wherein the 3D OCTA data comprises the identified structural vasculature information.

18. The method of claim 17, wherein the single scan of the object follows a Lissajous, orthogonal, or parallel scanning pattern.

19. The method of claim 17, wherein the OCT data comprises a plurality of scan pairs of OCT data from a same location of the object.

20. The method of claim 17, further comprising:

generating a 3D visualization of the object based on the 3D OCTA data.

* * * * *